United States Patent
O'Sullivan et al.

(10) Patent No.: US 7,306,587 B2
(45) Date of Patent: Dec. 11, 2007

(54) ADJUSTABLE HANDLE FOR A MEDICAL DEVICE

(75) Inventors: Donagh D. O'Sullivan, Ballina-Killaloe (IE); Arthur T. Henry, Dublin (IE)

(73) Assignee: Wilson-Cook Medical Inc., Winston-Salem, NC (US)

( * ) Notice: Subject to any disclaimer, the term of this patent is extended or adjusted under 35 U.S.C. 154(b) by 116 days.

(21) Appl. No.: 11/114,207

(22) Filed: Mar. 31, 2005

(65) Prior Publication Data

US 2005/0222568 A1 Oct. 6, 2005

Related U.S. Application Data

(60) Provisional application No. 60/558,315, filed on Mar. 31, 2004.

(51) Int. Cl.
*A61B 18/04* (2006.01)
*A61B 18/00* (2006.01)

(52) U.S. Cl. .............. 606/1; 606/111; 606/113
(58) Field of Classification Search ............ 606/1, 606/10–13, 127
See application file for complete search history.

(56) References Cited

U.S. PATENT DOCUMENTS

| | | | |
|---|---|---|---|
| 3,828,790 A | | 8/1974 | Curtiss et al. |
| 4,256,113 A | * | 3/1981 | Chamness .............. 606/47 |
| 4,467,802 A | * | 8/1984 | Maslanka ............. 606/206 |
| 5,084,054 A | * | 1/1992 | Bencini et al. ......... 606/113 |
| 5,620,459 A | * | 4/1997 | Lichtman ............. 606/205 |
| 5,904,693 A | * | 5/1999 | Dicesare et al. ........ 606/143 |
| 5,976,164 A | * | 11/1999 | Bencini et al. ......... 606/170 |
| 6,162,207 A | | 12/2000 | Ouchi et al. |
| 6,557,426 B2 | * | 5/2003 | Reinemann et al. ... 73/862.393 |
| 6,676,668 B2 | * | 1/2004 | Mercereau et al. ..... 606/127 |
| 6,905,057 B2 | * | 6/2005 | Swayze et al. ........ 227/176.1 |
| 2003/0109888 A1 | * | 6/2003 | Mercereau et al. ..... 606/127 |
| 2005/0060016 A1 | * | 3/2005 | Wu et al. .............. 623/1.11 |

FOREIGN PATENT DOCUMENTS

EP 0 446 020 A1 9/1991

OTHER PUBLICATIONS

International Search Report dated Jul. 19, 2005 for PCT Application No. PCT/US2005/011001.

\* cited by examiner

*Primary Examiner*—Henry M Johnson, III
(74) *Attorney, Agent, or Firm*—Brinks Hofer Gilson & Lione

(57) ABSTRACT

A handle for a medical device comprises a frame, a transmission, a slide, a first rack, a sheath, and a cable assembly. The transmission is mounted to the frame. The slide is moveably attached to the frame and coupled with the transmission. The first rack is moveably attached to the frame and coupled with the transmission. The sheath is secured to the first rack. The cable assembly is secured to the frame and extends through the sheath.

15 Claims, 5 Drawing Sheets

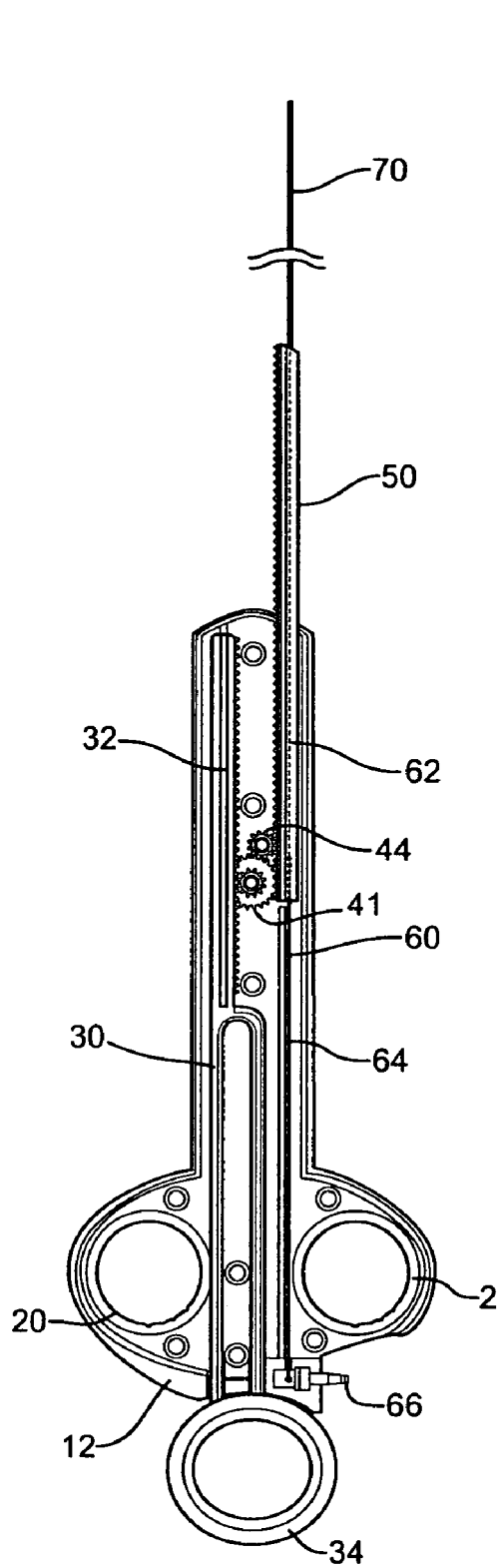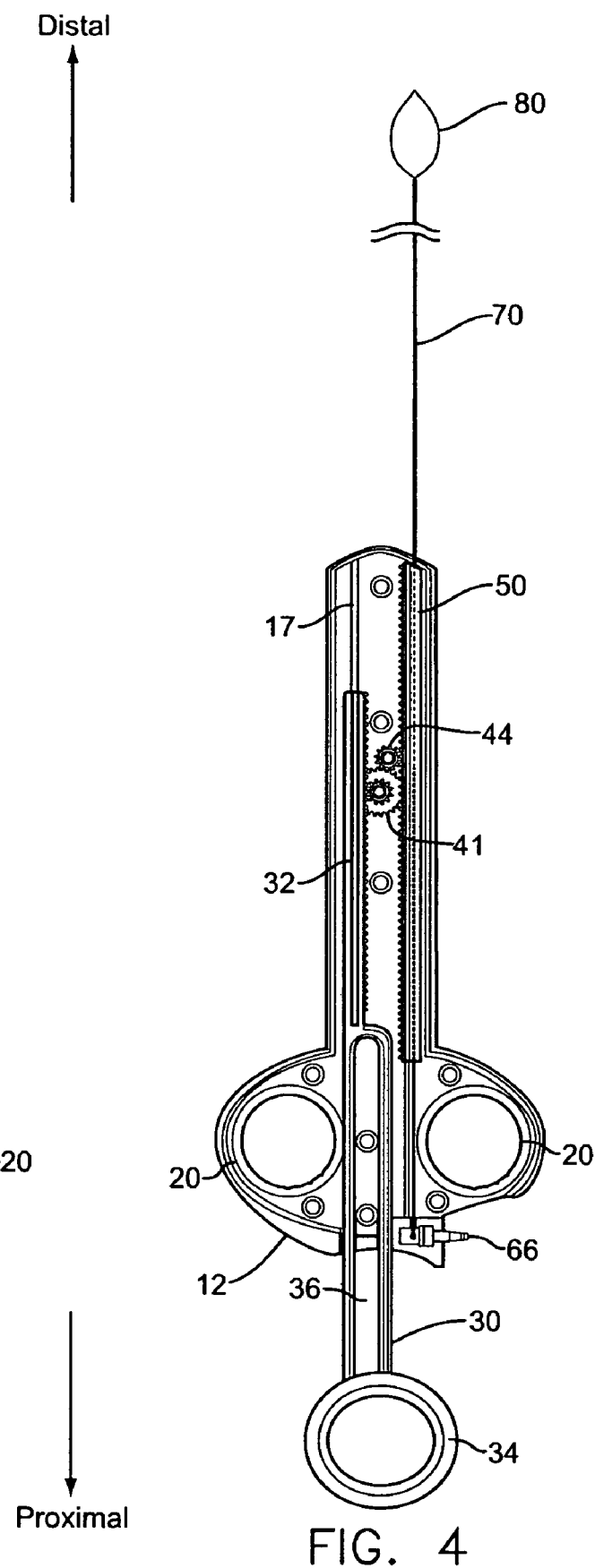
FIG. 3
FIG. 4

ADJUSTABLE HANDLE FOR A MEDICAL DEVICE

CLAIM FOR PRIORITY

The present application claims priority from U.S. Provisional Application Ser. No. 60/558,315, filed Mar. 31, 2004, which is fully incorporated herein.

TECHNICAL FIELD

This invention relates to a surgical instrument and more particularly, to an adjustable handle for a medical device that is introduced into body cavities and manually operated.

BACKGROUND

Medical devices generally have a need for improved actuation. While handles with an improved tactile feel have been available, they usually have a one-to-one activation ratio. In such cases, the actuating element of the handle moves the same amount as the working or gripping element of the device. For example, in gastroenterology, a medical device such as a snare may be used to surgically remove polyps from the colon. In such a procedure, it may be necessary for the snare to move from three to eleven centimeters. Moving the actuating element of the handle this same distance, referred to as the "throw" of the instrument, can be very uncomfortable for a surgeon. For those with small hands, handles requiring large throws can be especially difficult to operate, sometimes requiring two hands.

A snare is an electrically conductive loop of wire or cable that operates by electrically cutting and coagulating tissue that needs to be removed from the body. A typical surgical snare comprises an elongated flexible sheath connected at its proximal end to a handle. An elongated flexible cable extends through the sheath, with the proximal end of the cable connected to a movable portion of the handle so that the cable can be retracted and protracted by the surgeon relative to the sheath. An operating loop or snare is connected to the distal end of the cable. A surgeon opens and closes the loop by actuating the movable portion of the handle to protract or retract the cable. When the cable is in its protracted or forward position, the operating loop is outside the sheath and in its fully extended position for snaring, for example, a polyp. A polyp is a pre-cancerous tissue growth in the colon and rectum. As the cable is retracted, the loop is drawn into the sheath and closed.

A snare is inserted through a working channel of an endoscope fitted with a fiber optic camera. In addition to removing polyps, a snare can be used to surgically remove esophageal carcinoma or to perform nephrostomy. To excise a polyp, a doctor first manipulates an endoscope in the tract of the patient until the polyp is located. The end of the snare is extended from an insulating sheath and positioned around the polyp. The snare is then retracted, resecting the polyp. High frequency electrical current, such as radio frequency (RF) current, may be applied to the loop to cauterize the polyp and prevent bleeding.

Attempts have been made to provide a handle with a mechanical advantage that moves only a fraction of the distance of the snare travel. These handles have been complex assemblies with expensive manufacturing costs. In addition, due to friction between the moving parts and the complexity of the assemblies, some of these handles suffer from reduced tactile sensitivity, making it more difficult for the surgeon to operate. Furthermore, some of these handles use an actuating member to drive the cable and snare, while keeping the sheath stationary. Other handles actuate both the sheath and cable in opposite axial directions. This has the effect of pulling the snare into the sheath as the handle is actuated, which may not be appropriate depending on the circumstances. What is needed is a better handle for deploying a snare during endoscopic procedures.

BRIEF SUMMARY

Accordingly, embodiments of the present invention provide a new and improved handle for a surgical instrument. In one embodiment, the throw required to actuate the instrument is reduced or increased, depending on user need. The handle is cost efficient to manufacture and may be used as a disposable, one-time-use device. The handle can be easily adapted to provide increased or reduced throws, and is easier to use by virtue of the modified throw for operation. The improved handle operates by actuating a sheath over a fixed cable.

According to a first aspect of the invention, a handle for a medical device comprises a frame, a transmission, a slide, a first rack, a sheath, and a cable assembly. The transmission is mounted to the frame. The slide is moveably attached to the frame and coupled with the transmission. The first rack is moveably attached to the frame and coupled with the transmission. The sheath is secured to the first rack. The cable assembly is secured to the frame and extends through the sheath.

According to a second aspect of the invention, a handle for a medical device comprises a frame, a gear assembly, a slide, a first rack, a sheath, and a cable assembly. The gear assembly is rotatably mounted to the frame and has a first gear operably coupled with a second gear. The gear assembly has a mechanical advantage that is determined by a parameter of the first gear relative to a parameter of the second gear. The first rack is operably coupled with the first gear and slidably engaged with the frame. The slide is moveably attached to the frame and has a second rack that is operably coupled with the second gear and slidably engaged with the frame. The sheath is secured to the first rack and the cable assembly extends through the sheath and is secured to the frame.

A third aspect of the invention is a method of manufacturing a handle for a medical device. The method includes the steps of providing a frame and mounting a gear assembly having a mechanical advantage to the frame. The method also includes the step of slidably mounting a slide to the frame, where the slide is operatively coupled with the gear assembly. The method also includes the steps of securing a cable assembly to the frame and slidably mounting a moveable rack to the frame, where the moveable rack is operatively coupled with the gear assembly. The method also includes the step of attaching a sheath to the moveable rack, where the cable assembly extends coaxially through the sheath and where the sheath is retracted and protracted relative to the frame as the slide is actuated.

BRIEF DESCRIPTION OF THE DRAWINGS

FIG. 3 is a top view of the handle shown with the upper frame removed, illustrating the sheath protracted over the snare;

FIG. 4 is a top view of the handle shown with the upper frame removed, illustrating the sheath partially retracted from the snare;

DETAILED DESCRIPTION OF THE DRAWINGS AND THE PRESENTLY PREFERRED EMBODIMENTS

Figure 1:
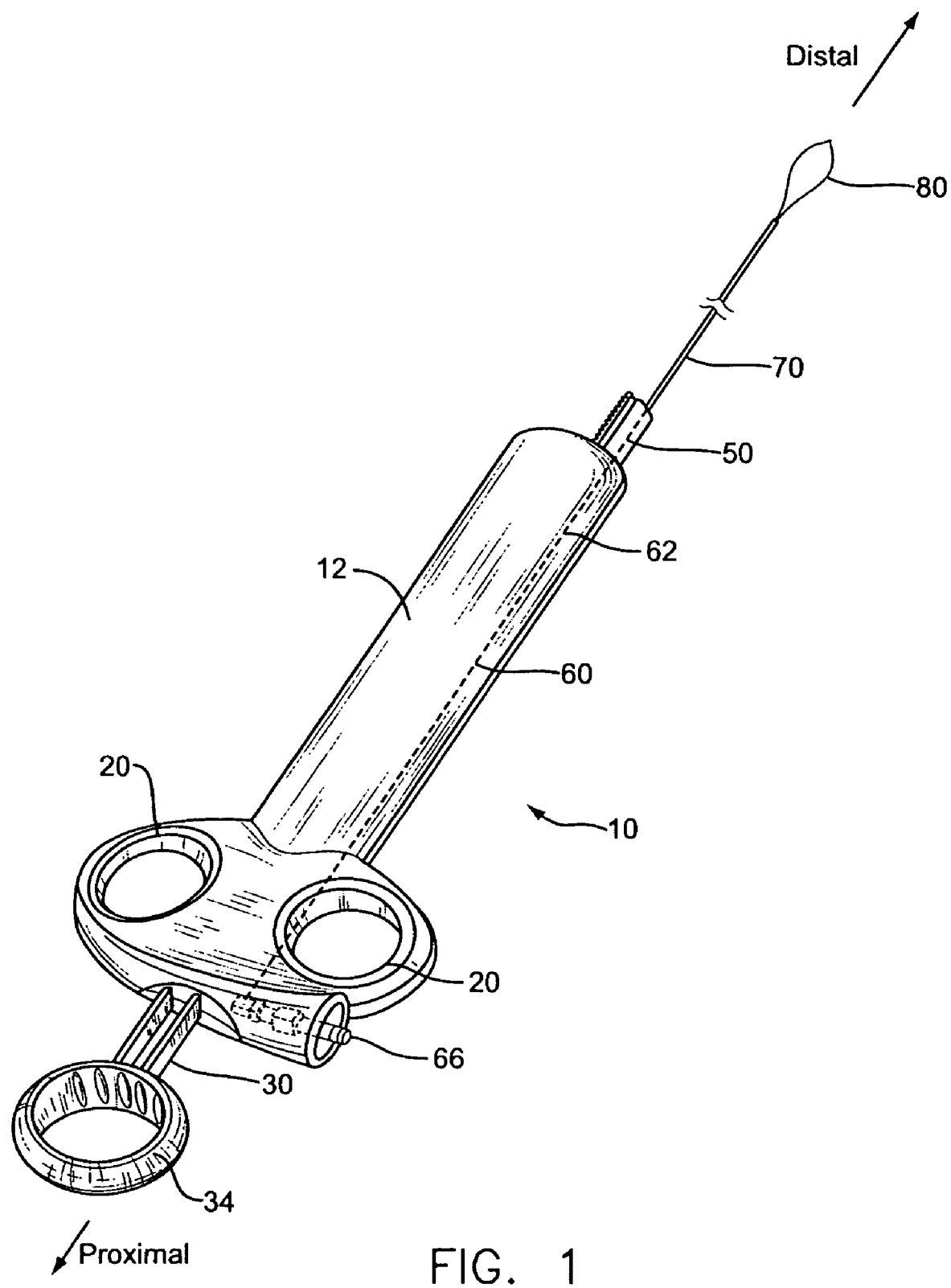
FIG. 1 is a perspective view of the handle showing the sheath in a partially retracted position.
Figure 2:
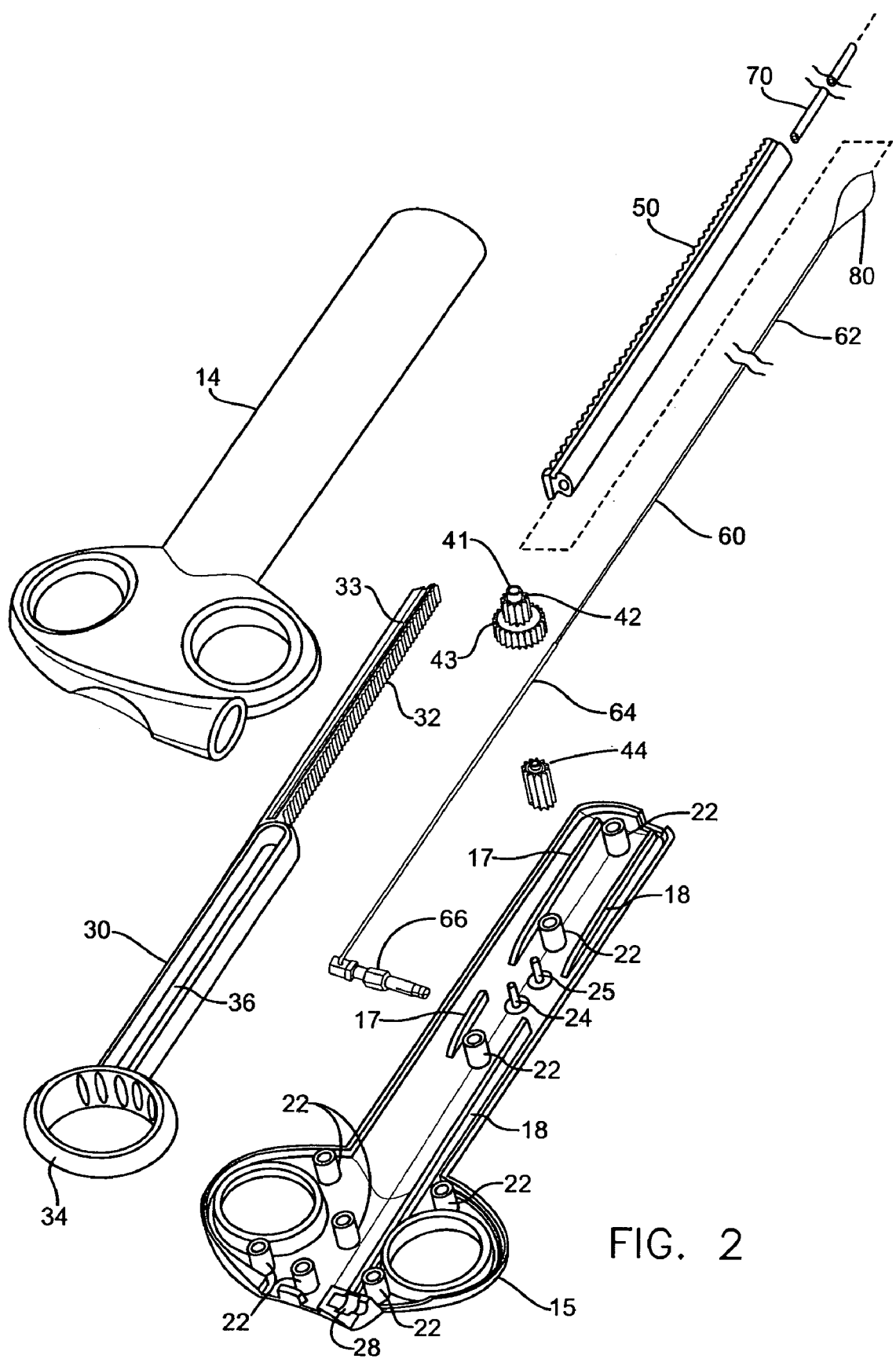
FIG. 2 is an exploded view of the handle.

FIGS. 1 and 2 disclose a handle 10 and a snare 80 for a medical device. The handle 10 includes a frame 12, a sheath 70, a slide 30, a gear assembly, a moveable rack 50, and a cable assembly 60 with cable 62. A thumb ring 34 is at the proximal end of handle 10. Snare 80 is mounted to the distal end of cable 62.

The frame 12 is made up of an upper frame 14 and a lower frame 15, with lower frame 15 connected to upper frame 14 with a snap fit or an interference fit, although other means of joining the two parts may be used. Handle 10 preferably includes finger rings 20 disposed on opposite sides of and integrally formed with frame 12. Bosses or locators 22 are integrally formed with lower frame 15 and mate with corresponding locators (not shown) integrally formed with upper frame 14 to align and join lower frame 15 with upper frame 14.

Handle 10 also includes slide 30 that fits and slides within frame 12. As shown in FIG. 2, slide 30 includes thumb ring 34 at the proximal end and a driving rack 32 at the distal end. Slide 30 also has a slot 36 formed between thumb ring 34 and driving rack 32. Driving rack 32 may be integrally formed with slide 30, and preferably is a bar with teeth on a face for gearing with a pinion or a gear to transform linear motion to rotary motion. Slide 30 is assembled such that two locators 22 integrally formed with lower frame 15 are positioned within slot 36. Locators 22 positioned within slot 36 constrain the movement of slide 30, serving to both align the movement of slide 30 within frame 12 and to restrain the movement of slide 30 such that it cannot be slidably removed from frame 12. As shown in FIG. 2, an integral groove 33 is formed along the top side of the driving rack 32. Not shown, an integral groove is also formed along the bottom side of driving rack 32. Slide rails 17 are integrally formed on the inside surfaces of upper frame 14 and lower frame 15. As slide 30 is moved into and out of frame 12, driving rack 32 slides over rails 17 on integral grooves 33.

Figure 6:
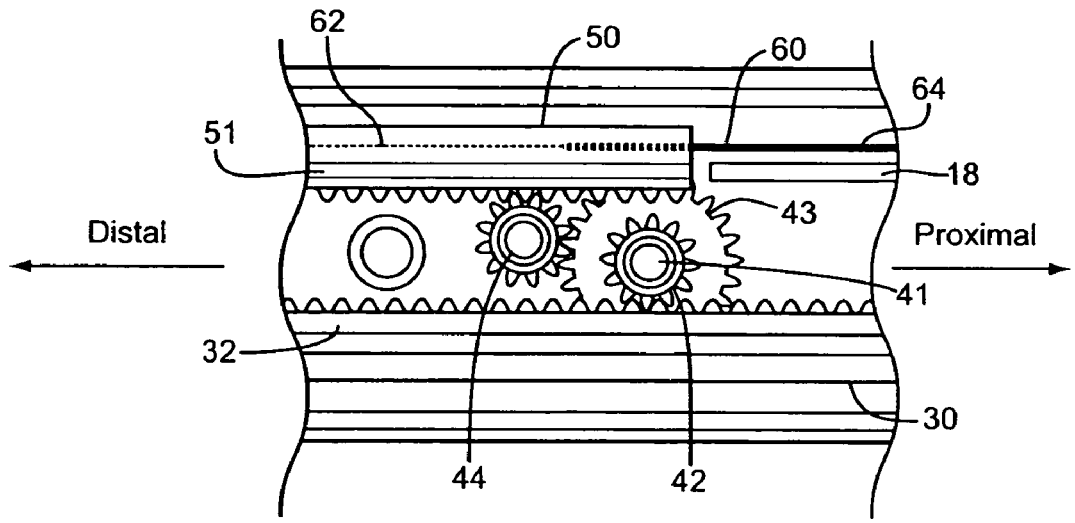
FIG. 6 is a detail top view of the gear assembly in FIG. 3.

As seen in FIGS. 3, 4, and 6, driving rack 32 engages and drives a transmission preferably consisting of a gear assembly made up of coupled gears. The gear assembly consists of a double gear 41, made up of a smaller first gear 42 and a larger second gear 43, and a third gear 44. Double gear 41 may be integrally formed, with first gear 42 and second gear 43 concentrically aligned, sharing an axis of rotation, and rotating at the same angular velocity, but operating in different planes. Double gear 41 is mounted and rotates about a first axle 24 integrally formed with frame 12 (see FIG. 3). Third gear 44 is mounted and rotates about a second axle 25 integrally formed with frame 12. Driving rack 32 directly engages the first gear 42 of double gear 41, which in turn rotates second gear 43, which engages and rotates third gear 44. Third gear 44 engages moveable rack 50, causing moveable rack 50 to translate distally or proximally, which in turn drives a sheath 70 to enclose or release snare 80. The gear assembly described above preferably uses a series of coupled spur gears operating in parallel planes. However, the gears may also operate in intersecting or skew planes, where bevel, helical, hypoid, or other suitable gears would then be used to couple slide 30 to moveable rack 50.

Figure 5:
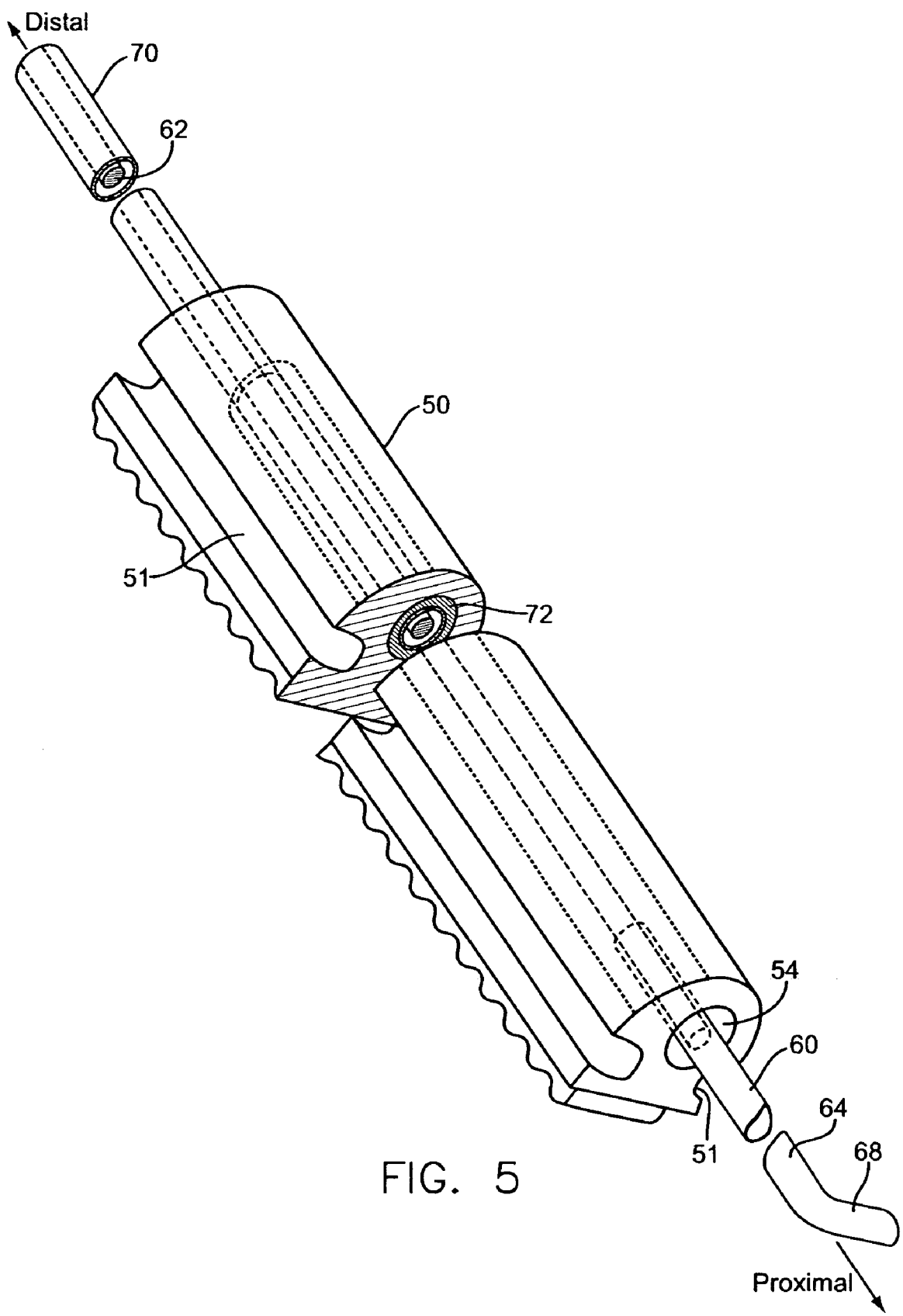
FIG. 5 is a perspective view showing the cable assembly, sheath, and moveable rack.

As seen in FIG. 5, an integral groove 51 is formed along the top side of moveable rack 50. A corresponding integral groove 51 is also formed along the bottom side of moveable rack 50. Grooves 51 constrain moveable rack 50 such that it slides along and is aligned by corresponding moveable rack rails 18 that are formed on the inside surfaces of upper frame 14 and lower frame 15. In addition, as seen in FIG. 5, a bore 54 runs through the length of moveable rack 50. Bore 54 is preferably a tapered through-hole, with a larger diameter at the proximal end of moveable rack 50 and a smaller diameter at the distal end.

Cable assembly 60, illustrated in FIGS. 2 and 5, is immovably attached to frame 12. Cable assembly 60 runs through bore 54 in moveable rack 50, and extends distally from frame 12. Bore 54 allows cable assembly 60 to run through moveable rack 50 into sheath 70. As moveable rack 50 is actuated, moving sheath 70 with respect to frame 12, cable assembly 60 remains immovably attached to frame 12. Cable assembly 60 includes cable 62, which is preferably elongated and flexible. Cable 62 is also preferably electrically conductive, such as a solid wire or braided cable of stainless steel, but may have rigid portions. A preferred cable has a diameter of approximately 0.75 mm, although other cable diameters may be used.

Figure 7:
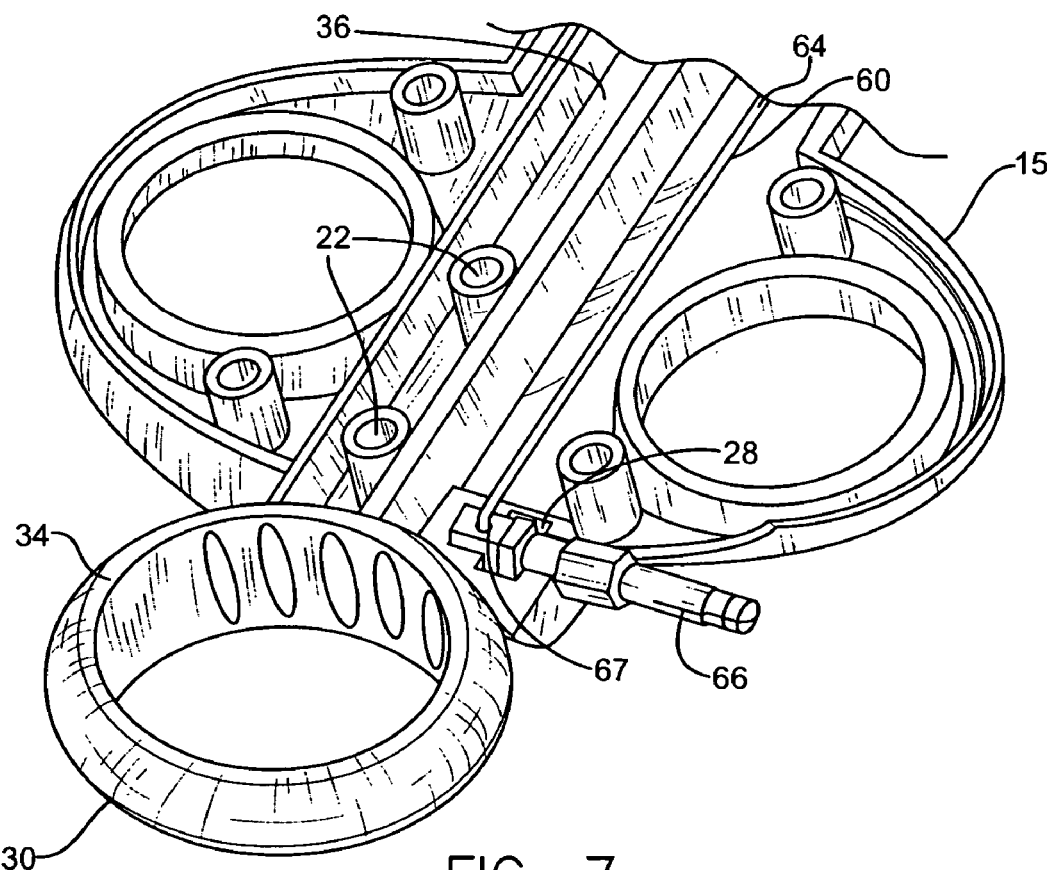
FIG. 7 is a detail perspective view of the slide, lower frame, and plug in FIG. 3.

A proximal end of cable 62 is attached to a rigid tube 64. Rigid tube 64 is preferably formed from stainless steel grade 304 tubing, approximately 1.1 mm in diameter and 15 cm long, and crimped onto cable 62. Other methods of connecting rigid tube 64 to cable 62 may be used, such as soldering or brazing. A short length 68 at the proximal end of rigid tube 64, approximately 4-5 mm, is bent at a 90° angle and is inserted into an orifice 67 located in the plug 66, as illustrated in FIG. 7. Rigid tube 64 may be secured to plug 66 by soldering, brazing, a set screw, a friction fit, or any other technique suitable for an electrical connection. Plug 66 is positioned in a plug recess 28 integrally formed on the inner surfaces of frame 12. For clarity, FIGS. 3, 4, and 7 illustrate plug 66 positioned in plug recess 28 in lower frame 15, with upper frame 14 shown removed. However, during assembly, it is preferable to first position plug 66 in a plug recess in upper frame 14 (not shown), and then attach rigid tube 64 to orifice 67 in plug 66. As upper frame 14 is placed over lower frame 15, plug 66 is immovably secured in plug recess 28. Additionally, a friction fit or minimal clearance fit between the inner surfaces of frame 12 and rigid tube 64 prevents rigid tube 64 from detaching out of orifice 67 in plug 66, providing additional security. Rigid tube 64 extends into bore 54 in moveable rack 50, so that a length of rigid tube 64 remains within bore 54, regardless of the relative position of moveable rack 50 with respect to frame 12.

As seen in FIG. 2, the distal end of cable assembly 60 may terminate in a snare 80. For example, a snare such as the AcuSnare® from COOK®, Wilson-Cook Medical Inc., GI Endoscopy, Winston-Salem, N.C., USA, can be attached to the distal end of cable 62. However, other types of gripping elements or working elements, such as baskets, grasping forceps, angled snare loops, or point-type cauterization devices can be substituted for snare 80. In the embodiment disclosed herein, an electrical current, such as RF (radio frequency) electrical current, may be applied to plug 66. The current is conducted along rigid tube 64 to cable 62 to snare 80, to electrically cauterize a polyp. If an electrical current is applied, however, the cable assembly 60 and snare 80 must be electrically insulated by sheath 70 (described below) and frame 12, preventing inadvertent electrocution to either the patient or user.

As seen in FIG. 5, a proximal end of sheath 70 is secured to moveable rack 50. Sheath 70 is preferably an elongated flexible tube made from a length of PTFE (polytetrafluoroethylene) or Teflon® tubing. Sheath 70 may also be made from any flexible lubricious material that does not conduct electricity, such as polyimide tubing. Cable assembly 60 and sheath 70 are coaxially aligned, such that sheath 70 covers cable assembly 60. Sheath 70 can be secured to bore 54 of moveable rack 50 through a friction fit, such as by crimping an external metal ring 72 to the outer diameter of sheath 70, and then press fitting that assembly into bore 54 of moveable rack 50. For greater attachment strength, a metal ring (not shown) may also be placed inside the inner diameter of sheath 70 before external metal ring 72 is crimped onto sheath 70. Sheath 70 is preferably sized with an outer diameter of approximately 2.3 to 2.4 mm and an inner diameter of approximately 1.5 to 1.6 mm. Alternatively, the inner diameter of sheath 70 is sized to enable cable assembly 60 and snare 80 to have substantially free longitudinal movement along the entire length of sheath 70.

Frame 12, slide 30, the gears in the gear assembly, and moveable rack 50 may be made from any medically suitable, and preferably electrically insulating, material. To make handle 10 inexpensive and disposable, frame 12, slide 30, the gears, and moveable rack 50 may be molded from a suitable plastic such as polycarbonate, acetal, or ABS (acrylonitrile-butadiene-styrene). Frame 12 may be injection molded as a clam shell with upper frame 14 and lower frame 15 separately injection molded and joined later by melting, snap fitting, or applying a medically acceptable adhesive, such as cyanoacrylate.

In addition, a biocompatible silicone type lubricant may be used to reduce friction on the gears, first axle 24, second axle 25, slide rails 17, moveable rack rails 18, the inner diameter of sheath 70, or any other moving parts.

Referring now to FIGS. 3, 4, and 6, as slide 30 is pressed into frame 12 with thumb ring 34 in a distal direction, driving rack 32 drives first gear 42 of double gear 41 clockwise. As second gear 43 is axially connected to first gear 42, second gear 43 is also rotated clockwise, which in turn rotates third gear 44 counterclockwise. This counterclockwise rotation of third gear 44 drives moveable rack 50, causing it to move distally away from frame 12, which is upward in FIG. 4 and to the left in FIG. 6. As sheath 70 is secured to moveable rack 50, sheath 70 also moves distally away from frame 12. Because cable assembly 60 is immovably attached to the proximal end of frame 12, cable assembly 60 does not move relative to frame 12, and sheath 70 is protracted over cable assembly 60 and snare 80, covering snare 80 as shown in FIG. 3. Pulling slide 30 and thumb ring 34 away from frame 12 reverses this action, causing sheath 70 to be retracted from cable assembly 60 and snare 80, exposing snare 80, as shown in FIG. 4.

Parameters of first gear 42 and second gear 43, such as the outer diameters or the radii, may be selected so that a desired mechanical advantage is achieved, where the displacement or movement of slide 30 relative to frame 12 is a particular ratio to the displacement or movement of moveable rack 50 and sheath 70. A gear ratio of 1:2 is illustrated in FIGS. 3 and 4. In such a case, a surgeon would only need to move thumb ring 34 about 5 cm to achieve a 10 cm displacement of sheath 70 and moveable rack 50 relative to snare 80. However, the sizes of the gears can be selected so that other mechanical advantages are achieved, such as 1:4, 2:1, or 4:1, providing for reduced or increased handle throws as appropriate. In addition, third gear 44 can be eliminated, with moveable rack 50 directly engaging second gear 43. In such a case, as slide 30 is pressed into frame 12, moveable rack 50 and sheath 70 would move in an opposite direction to slide 30, retracting moveable rack 50 and sheath 70 and exposing cable assembly 60 and snare 80.

As snares or other gripping or working elements are sold in a wide range of sizes, a sheath may have to be displaced widely varying distances relative to the snare. Accordingly, the stroke length of a slide in a handle may be adjusted to accommodate the different stroke lengths required to fully actuate the various snares or other working elements. During assembly, the manufacturer can control the total stroke length that the slide must move relative to the frame for retracting or protracting the sheath. Before upper frame 14 is connected to lower frame 15, the slide 30 and moveable rack 50 can be placed on slide rails 17 or moveable rack rails 18, respectively, at different starting positions along the rails. After the gears and other interconnected components are coupled with driving rack 32 and moveable rack 50, the stroke length is set.

In operating handle 10, a user grasps thumb ring 34 and finger rings 20 and pushes thumb ring 34 into frame 12. As seen in FIG. 3, in this fully protracted position, sheath 70 is protracted over cable assembly 60 and snare 80. In one application, a surgeon would insert the distal end of sheath 70 through the working channel of an endoscope into a patient's colon until the polyp is located. Using one hand, the surgeon could then pull thumb ring 34 away from finger rings 20 (illustrated in FIG. 4) causing sheath 70 to retract from snare 80, exposing and opening snare 80 so that it can be used to snare the patient's polyp. After the snare is positioned around the polyp, the surgeon would then push the thumb ring 34 back into the frame 12. This causes the sheath to protract over snare 80, closing snare 80 around the polyp. With the 1:2 gear ratio disclosed in FIG. 6, a surgeon would only need to move thumb ring 34 about 5 cm to achieve a 10 cm displacement of sheath 70 and moveable rack 50 relative to snare 80.

While the invention has been described with reference to details of the illustrated embodiment, these details are not intended to limit the scope of the invention as defined in the appended claims. For example, in place of a gear assembly, the handle may use another type of transmission to create a mechanical advantage. A transmission made up of levers in a linkage system, pulleys, or a hydraulic or pneumatic actuator may also be used to transfer a mechanical advantage from the slide to the sheath. For a linkage system, a distal end of the slide may be attached to one point along a lever, with a proximal end of the sheath attached to another point along the lever. A pivot may be placed along the lever so that a desired mechanical advantage is achieved. If a pulley system is used, the slide may be connected to a pulley that is slidably attached to the frame. A flexible pulley cable capable of transmitting both tensile and compressive forces may wrap around the pulley, connected to the sheath at one end and secured to the frame at another end. Alternately, a hydraulic or pneumatic actuator may be used to create the desired mechanical advantage. It may be desired to use one or more hydraulic or pneumatic actuators in a push-pull arrangement, with one or more actuators pushing the sheath relative to the frame, and one or more actuators pulling the sheath relative to the frame. The mechanical advantage would be controlled by adjusting the hydraulic or pneumatic diameters of the actuators.

In addition, the handle can be used for surgical instruments other than snares. In fact, the handle can be used in connection with any surgical instrument having first and second coaxial members, such as retrieval baskets, irrigation systems, and graspers, among others. All such devices are meant to be included by the following claims.

We claim:

1. A handle for a medical device comprising:
a frame enclosing a transmission and a driving second rack, said transmission being mounted to the frame and said driving second rack moveably attached to the frame and coupled with the transmission,
a moveable first rack at least partially enclosed within the frame, said moveable first rack being moveably attached to the frame and coupled with the transmission;
a sheath secured to the moveable first rack; and
a cable assembly secured to the frame and extending through the sheath;
wherein the transmission further comprises a gear assembly having a first gear operably coupled with a second gear, with the moveable first rack operably coupled with the first gear and slidably engaged with the frame, and the driving second rack operably coupled with the second gear and slidably engaged with the frame; and wherein the transmission has a predetermined mechanical advantage determined by a parameter of the first gear relative to a parameter of the second gear; and
wherein the first gear or the second gear is a double gear.

2. The handle of claim 1, wherein the sheath is elongated and flexible, the cable assembly is elongated and flexible, and the cable assembly further comprises a snare attached to a distal end of the cable assembly.

3. The handle of claim 2, wherein movement of the sheath a predetermined distance relative to the frame encloses or releases the snare.

4. The handle of claim 1, wherein the predetermined mechanical advantage is not equal to one.

5. The handle of claim 1, wherein the moveable first rack has a bore extending through the moveable rack and the cable assembly extends through the bore.

6. The handle of claim 1, wherein the cable assembly further comprises: an elongated flexible cable; a rigid tube attached coaxially to a proximal end of the elongated flexible cable; and a plug attached to a proximal end of the rigid tube.

7. The handle of claim 1, wherein the cable assembly is capable of transmitting an electrical cauterizing current, and the sheath and the frame electrically insulate the cable assembly.

8. The handle of claim 1, further comprising at least one finger ring mounted to the frame, wherein the at least one finger ring is integral with the frame.

9. The handle of claim 1, wherein the slide further comprises a thumb ring, wherein the thumb ring is integral with the driving second rack.

10. A handle for a medical device comprising:
a frame;
a transmission mounted to the frame;
a slide moveably attached to the frame and coupled with the transmission, wherein the slide further comprises a second rack, and wherein the transmission further comprises a gear assembly having a first gear operably coupled with a second gear, with the first rack operably coupled with the first gear and slidably engaged with the frame, and the second rack operably coupled with the second gear and slidably engaged with the frame; and wherein the transmission has a predetermined mechanical advantage determined by a parameter of the first gear relative to a parameter of the second gear;
the first rack moveably attached to the frame and coupled with the transmission;
a sheath secured to the first rack; and
a cable assembly secured to the frame and extending through the sheath, and wherein the gear assembly further comprises a third gear operably coupled between the first rack and the first gear, and the slide translates in the same direction as the first rack.

11. A handle for a medical device comprising:
a frame;
a gear assembly rotatably mounted to the frame having a first gear operably coupled with a second gear and with a mechanical advantage determined by a parameter of the first gear relative to a parameter of the second gear;
a first rack operably coupled with the first gear and slidably engaged with the frame;
a slide moveably attached to the frame, having a second rack operably coupled with the second gear and slidably engaged with the frame;
a sheath secured to the first rack; and a cable assembly secured to the frame and extending through the sheath; and
wherein the gear assembly further comprises a third gear operably coupled between the first rack and the first gear, and the slide translates in a same direction as the first rack.

12. The handle of claim 11, wherein the sheath is elongated and flexible, the cable assembly is elongated and flexible, and the cable assembly further comprises a snare attached to a distal end of the cable assembly.

13. The handle of claim 11, wherein the cable assembly further comprises: an elongated flexible cable; a rigid tube attached coaxially to a proximal end of the elongated flexible cable; and a plug attached to a proximal end of the rigid tube.

14. The handle of claim 11, wherein the cable assembly is capable of transmitting an electrical cauterizing current, and the sheath and the frame electrically insulate the cable assembly.

15. The handle of claim 11, further comprising at least one finger ring integrally mounted to the frame, and wherein the slide further comprises a thumb ring integral with the slide.

* * * * *